(12) United States Patent
Peitz et al.

(10) Patent No.: US 12,404,465 B2
(45) Date of Patent: Sep. 2, 2025

(54) PROCESS FOR REMOVING EXTRANEOUS ODOUR-FORMING SUBSTANCES FROM HYDROCARBON STREAMS

(71) Applicant: Evonik Oxeno GmbH & Co. KG, Marl (DE)

(72) Inventors: Stephan Peitz, Oer-Erkenschwick (DE); Guido Stochniol, Haltern am See (DE); Armin Matthias Rix, Marl (DE); Matthias Böse, Raesfeld (DE); Tanita Valèrie Six, Dortmund (DE); Martin Althoff, Marl (DE); Ralf Boll, Dorsten (DE); Helena Lopez-Fernandez, Herme (DE)

(73) Assignee: Evonik Oxeno GmbH & Co. KG, Marl (DE)

( * ) Notice: Subject to any disclaimer, the term of this patent is extended or adjusted under 35 U.S.C. 154(b) by 328 days.

(21) Appl. No.: 18/191,139

(22) Filed: Mar. 28, 2023

(65) Prior Publication Data

US 2023/0313054 A1    Oct. 5, 2023

(30) Foreign Application Priority Data

Mar. 29, 2022    (EP) ..................................... 22165010

(51) Int. Cl.
  *C07C 7/12*    (2006.01)
  *C07C 7/04*    (2006.01)
  (Continued)

(52) U.S. Cl.
  CPC ..... *C10G 65/04* (2013.01); *C10G 2300/1037* (2013.01); *C10G 2300/4081* (2013.01); *C10G 2400/28* (2013.01)

(58) Field of Classification Search
  CPC ............ C10G 65/04; C10G 2300/1037; C10G 2300/4081; C10G 2400/28; B01D 53/02;
  (Continued)

(56) References Cited

U.S. PATENT DOCUMENTS

| 6,538,168 | B1 | 3/2003 | Schwab et al. |
| 10,364,199 | B2 * | 7/2019 | Kuwana .................. C07C 7/163 |

(Continued)

FOREIGN PATENT DOCUMENTS

| EP | 1 069 101 | 1/2001 | |
| WO | WO-2014009159 A2 * | 1/2014 | ............. B01D 53/04 |

OTHER PUBLICATIONS

Extended European Search Report dated Oct. 12, 2022, in European Patent Application No. 22165010.4, 6 pages.
(Continued)

*Primary Examiner* — In Suk C Bullock
*Assistant Examiner* — Jason Y Chong
(74) *Attorney, Agent, or Firm* — Grüneberg and Myers PLLC

(57) ABSTRACT

A process can be used for purifying a hydrocarbon stream containing at least Cx alkanes, Cx olefins, low boilers such as Cx−1 hydrocarbons, and high boilers such as Cx+1 hydrocarbons, with x=3 or 4. The process involves separating off low boilers and separating off high boilers, wherein the separating-off of high boilers is performed in the presence of hydrogen and hence a hydrogenation of the olefins present takes place.

16 Claims, 2 Drawing Sheets

(51) Int. Cl.
    *C07C 7/163*      (2006.01)
    *C10G 65/04*      (2006.01)
(58) Field of Classification Search
    CPC .... B01D 53/04; B01D 2257/702; C07C 7/04;
                      C07C 7/12; C07C 7/163; C07C 5/03;
                                               C07C 9/08
    See application file for complete search history.

(56)            References Cited

U.S. PATENT DOCUMENTS 10,472,306 B1 *   11/2019   Frey ..................... B01D 3/322
    2016/0347690 A1   12/2016   Peitz et al.
    2020/0216376 A1    7/2020   Peitz et al.

OTHER PUBLICATIONS

U.S. Appl. No. 16/713,301, filed Dec. 13, 2019, 2020/0216376, Peitz et al.

* cited by examiner

PROCESS FOR REMOVING EXTRANEOUS ODOUR-FORMING SUBSTANCES FROM HYDROCARBON STREAMS

CROSS-REFERENCE TO RELATED APPLICATIONS

This application claims priority to European Application No. 22165010.4, filed on Mar. 29, 2022, the content of which is hereby incorporated by reference in its entirety.

BACKGROUND OF THE INVENTION

Field of the Invention

The invention provides a process for purifying a hydrocarbon stream comprising at least medium boilers such as Cx alkanes, Cx olefins, low boilers such as Cx−1 hydrocarbons and high boilers such as Cx+1 hydrocarbons, with x=3 or 4. The process comprises separating off low boilers and separating off high boilers, wherein the treatment of the remaining medium boilers is conducted in the presence of hydrogen and hence a hydrogenation of the olefins present and very substantial removal of further unwanted substances takes place.

Description of Related Art

The removal of unwanted and/or odour-forming substances is an indispensable step especially for propellant gases for cosmetic or medical use, i.e. usually low molecular weight alkanes such as propane, isobutane or n-propane. The term "odour-forming substance" in this connection is any substance or compound not corresponding to the substance that constitutes the propellant gas. Any contamination with reactive components such as olefins, but also any odour contamination with other substances or compounds, must be avoided since the compositions are usually applied to the body.

There are various processes in the literature for purification of propellant gases such as propane, isobutane or n-butane. It is often the case that various sorption variants are used, for example adsorption via an adsorber such as activated carbon, in which a gas stream is passed over the adsorber and hence particular substances are adsorbed by the adsorber and hence removed from the gas stream. The term "sorption" in the context of the present invention includes both physisorption and chemisorption, since these two modes of sorption cannot always be clearly separated from one another.

However, the problem with the known sorption methods is that the adsorbers used have to be cleaned again with time in order to drive out the adsorbed substances again. This can entail both frequent adsorber changes and high regeneration and procurement costs for the adsorber. Furthermore, additional hydrogenation of the olefins present in the raw material usually has to be undertaken, since these bind only inadequately to adsorbers and cannot be removed completely. In addition, it is necessary to remove both low boilers in a separation of low boilers and high boilers in a separate separation of high boilers, in order to obtain the desired chain length distribution in the propellant gas. As well as the high costs, all this leads to very complex and multistage processes with complex interconnection of plant components.

SUMMARY OF THE INVENTION

It was therefore an object of the present invention to provide a purification process with very simple interconnection of the respective plant components. In addition, a very inexpensive process was to be provided.

The object was achieved by the process described in the embodiments below. Preferred embodiments of the process are also specified below. The process according to the invention is a process for purifying a hydrocarbon stream comprising at least medium boilers such as Cx alkanes, $C_x$ olefins, low boilers such as $C_{x-1}$ hydrocarbons and high boilers such as $C_{x+1}$ hydrocarbons, where x=3 or 4, wherein the process comprises the following steps:
  a) separating off at least a portion of the low boilers and separating off at least a portion of the high boilers in a single distillation column to obtain a medium boiler intermediate;
  b) removing at least a portion of the remaining low boilers and/or at least a portion of the remaining high boilers from the medium boiler intermediate obtained from step a) by means of sorption in a sorption unit to obtain a purified hydrocarbon stream containing more than 98% by weight of $C_x$ alkanes, characterized in that
  the sorption in step b) is conducted in the presence of hydrogen, and in that a hydrogenation of at least a portion of the olefins present additionally takes place in the sorption unit.

The invention also includes the following embodiments:
  1. Process for purifying a hydrocarbon stream comprising at least $C_x$ alkanes, $C_x$ olefins, low boilers such as $C_{x-1}$ hydrocarbons and high boilers such as $C_{x+1}$ hydrocarbons, where x=3 or 4, wherein the process comprises the following steps:
     a) separating off at least a portion of the low boilers and separating off at least a portion of the high boilers in a single distillation column to obtain an intermediate;
     b) removing at least a portion of the remaining low boilers and/or at least a portion of the remaining high boilers from the intermediate obtained from step a) by means of sorption in a sorption unit to obtain a purified hydrocarbon stream containing more than 98% by weight of $C_x$ alkanes,
     characterized in that the sorption in step b) is conducted in the presence of hydrogen, and in that a hydrogenation of at least a portion of the olefins present additionally takes place in the sorption unit.
  2. Process according to embodiment 1, wherein the hydrocarbon stream used for purification is a C3 hydrocarbon stream.
  3. Process according to embodiment 1 or 2, wherein the distillation column consists of an upper section comprising the top of the distillation column and at least one separation stage, a middle section comprising at least one separation stage, and a lower section comprising the bottom of the distillation column and at least one separation stage.
  4. Process according to embodiment 3, wherein the distillation column is a dividing wall column having a dividing wall in the middle section, which divides the middle section into two separate parts: the feed section and the outlet section.
  5. Process according to embodiment 4, wherein the intermediate obtained from the separating-off in step a) is removed via a side draw in the outlet section of the distillation column.
  6. Process according to embodiment 4 or 5, wherein the hydrocarbon stream to be purified, from which the low boilers and the high boilers are at least partly removed, is fed in in the feed section of the dividing wall column.

7. Process according to any of the preceding embodiments, wherein a stream containing the low boilers is removed via the top of the column in the dividing wall column, and a stream containing the low boilers is removed via the bottom of the column.
8. Process according to embodiment 7, wherein the stream removed at the top that contains the low boilers is guided to a condenser, where it is at least partly condensed.
9. Process according to embodiment 8, wherein the uncondensed portion of the stream is discharged from the process.
10. Process according to embodiment 8 or 9, wherein the condensed portion of the stream is recycled to the dividing wall column.
11. Process according to embodiment 10, wherein the recycled condensed portion of the stream is introduced into the first separation stage of the upper section of the distillation column.
12. Process according to any of the preceding embodiments, wherein the hydrocarbon stream to be purified passes through a heat exchanger and is preheated before the stream is fed to the dividing wall column.
13. Process according to embodiment 12, wherein the heating in the heat exchanger is effected by heat exchange with the intermediate.
14. Process according to any of the preceding embodiments, wherein a sorbent comprising a porous carrier material, especially $SiO_2$, coated with nickel and tin oxide on its surface is used in the separating-off in step b).
15. Process according to embodiment 14, wherein the sorbent has the following composition that adds up to 100% by weight:
   nickel: 15% to 65% by weight;
   zinc oxide: 5% to 40% by weight;
   silicon dioxide: 5% to 75% by weight;
   graphite: 0% to 5% by weight;
   other components 0% to 1% by weight.

DETAILED DESCRIPTION OF THE INVENTION

Figure 1:
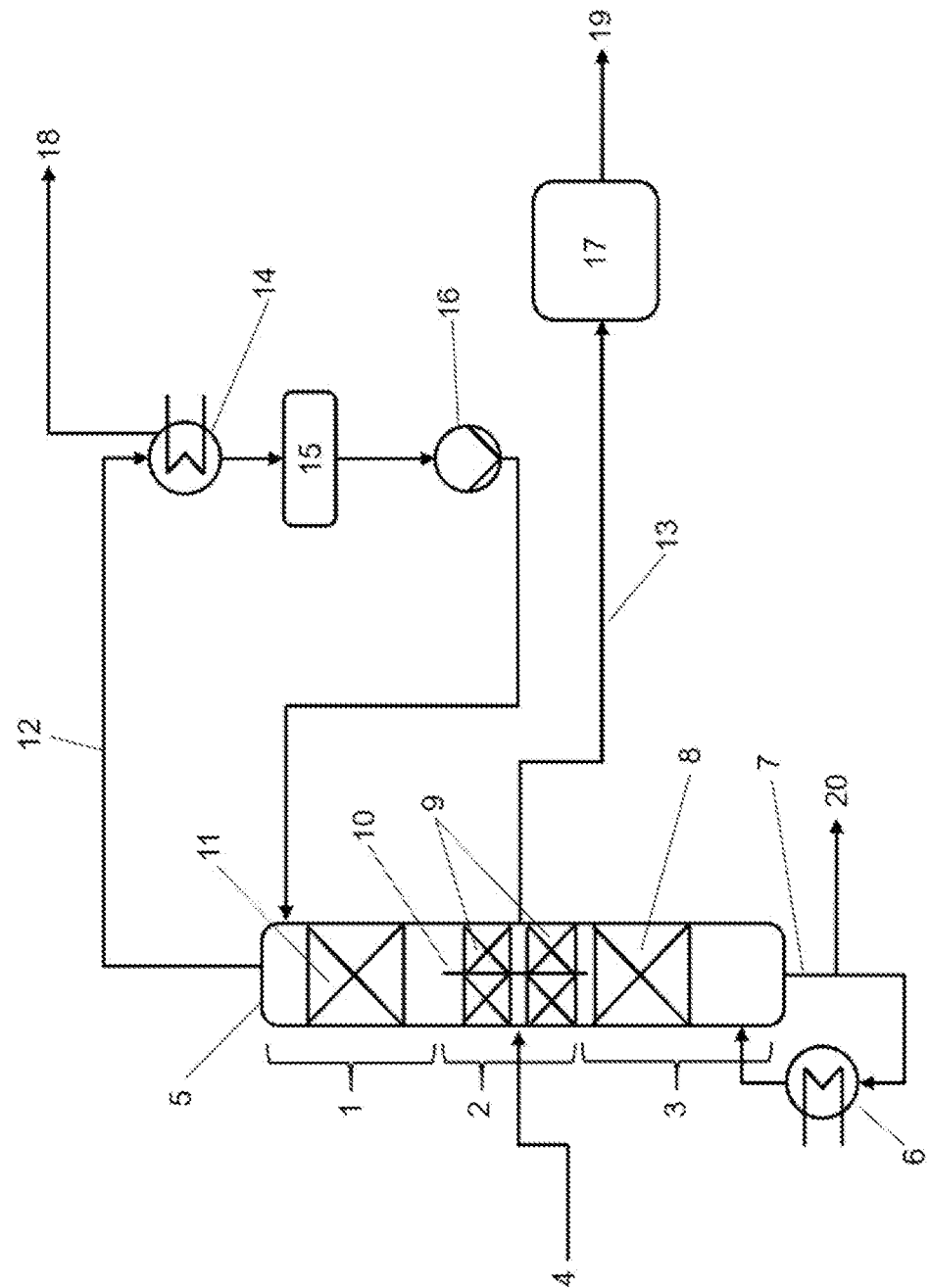
FIG. 1 shows an embodiment of the present invention with a distillation column for the separating-off in step a) and a sorption unit for the sorption in step b).

The hydrocarbon stream to be purified is a $C_x$ hydrocarbon stream with x=3 or 4. Such streams contain both $C_x$ alkanes and $C_x$ olefins, but also low boilers such as $C_{x-1}$ hydrocarbons and high boilers such as $C_{x+1}$ hydrocarbons. Such streams are available on an industrial scale and are obtained, for example, as waste products in chemical processes, but on account of the presence of the low and high boilers and/or further undesirable substances can be utilized commercially or sold only with difficulty. In order to obtain streams containing more than 98% by weight of $C_x$ alkanes, the streams are purified in accordance with the invention.

The hydrocarbon stream to be purified is accordingly a C3 hydrocarbon stream or a C4 hydrocarbon stream. C3 hydrocarbon streams according to the invention contain at least propene, propane, C2 hydrocarbons (e.g. ethene, ethane) and C4 hydrocarbons (e.g. butane, butene). Such a C3 hydrocarbon stream is also referred to in the context of the present invention as propane stream (to be purified). C4 hydrocarbon streams according to the invention contain at least butene (e.g. 1-butene, 2-butene, possibly isobutene), butane, C3 hydrocarbons (e.g. propene, propane) and C5 hydrocarbons (e.g. pentene, pentane). Such a C4 hydrocarbon stream is also referred to in the context of the present invention as butane stream or isobutane stream (to be purified). In a preferred embodiment, the hydrocarbon stream used for purification is a propane stream.

The composition of the propane stream is fundamentally not limited to a particular composition. The only prerequisite is that the individual components as described are present. According to the invention, however, the propane stream may contain from 0.0001% up to 3% by weight of C2 hydrocarbons, from 0.01% up to 20% by weight of propene, and from 0.0001% up to 20% by weight of C4 hydrocarbons. In addition, the propane stream may additionally contain, inter alia, small amounts of methanethiol, ethanethiol, dimethyl sulfide, dimethyl disulfide and/or hydrogen sulfide (in each case up to 100 ppm by weight). The propane stream may contain further substances or compounds in traces, which cannot be enumerated individually. Some of these substances may have a perceptible odour. The presence thereof is unwanted and is minimized by the process described here.

In the first step a) of the process according to the invention, the hydrocarbon stream to be purified, especially the propane stream or the butane stream, is fed to a distillation column where at least a portion of the low boilers and at least a portion of the high boilers are separated off. This separating-off is effected in the same distillation column. It will be apparent that the low boilers present are obtained at the top and the high boilers present at the bottom. The hydrocarbon stream prepurified by the at least partial separating-off of low boilers and high boilers, called medium boiler intermediate here, may then especially be removed as sidestream or as medium boiler fraction.

The distillation column used for the separating-off of at least a portion of the low boilers and for the separating-off of at least a portion of the high boilers in step a) may in principle be configured as desired, provided that the function, i.e. the simultaneous separating-off of low and high boilers, is assured. In a preferred embodiment, the distillation column used in step a) consists of an upper section, a middle section and a lower section.

The upper section comprises the top of the distillation column, where a stream containing the low boilers is obtained, and at least one separation stage. A separation stage may comprise one or more separation trays, structured packings or beds of random packing, or combinations thereof. The stream obtained and removed at the top of the upper section of the distillation column, which contains the low boilers, is preferably guided to a condenser, where it is at least partly condensed. Both the uncondensed portion of the stream and the condensed portion of the stream each contain low boilers. The uncondensed portion is then at least partly discharged from the process, and may be guided, for example, into the offgas of chemical production plants. The condensed portion may still contain significant amounts of $C_x$ alkanes, Cx olefins or high boilers, and is therefore preferably recycled at least partly to the dividing wall column. It is preferable here when the recycled condensed portion of the stream is guided to or into the first separation stage of the upper section of the distillation column.

The middle section of the distillation column comprises at least one separation stage. A separation stage may comprise one or more separation trays, structured packings or beds of random packing, or combinations thereof. In a preferred embodiment of the present invention, the distillation column used in step a) is a dividing wall column, meaning that the distillation column has a dividing wall that extends vertically at least over part of the middle section of the distillation column. Preferably, the dividing wall extends vertically over the entire height of the middle section. The dividing wall divides the middle section at least partly into two mutually separate regions, one of which is referred to as feed section and the other as outlet section. The dividing wall thus runs radially from wall to wall within the column, in order to create the two separate regions. The feed section is defined in that the feed to the distillation column is present in this part of the middle section, through which the distillation column is fed with the hydrocarbon stream to be purified. The outlet section is defined in that the outlet from the distillation column is present in this part of the middle section, through which the medium boiler intermediate is removed from the distillation column. There is at least one separation stage both in the feed section and in the outlet section. However, it is also possible for there to be more than one separation stage each in the feed section and in the outlet section. The number of separation stages in the feed section and in the outlet section may be the same or different.

The middle section of the distillation column preferably has a side draw in the outlet section, where the intermediate from step a) is removed and is guided thence to the sorption in step b). Further preferably, the middle section of the distillation column contains a feed for the hydrocarbon stream to be purified, which is disposed in the feed section. Before entry into the distillation column, the hydrocarbon stream to be purified may pass through a heat exchanger. This preheats the stream to be purified before it is fed to the dividing wall column. The heating in the heat exchanger is preferably effected by heat exchange with the intermediate withdrawn from the distillation column. This has the advantage that the medium boiler intermediate is cooled before arriving in the sorption in step b), and also saves energy for the heating of the hydrocarbon stream to be purified.

The lower section comprises the bottom of the distillation column, where a stream containing the high boilers is obtained, and at least one separation stage. A separation stage may comprise one or more separation trays, structured packings or beds of random packing, or combinations thereof. The stream that has run downward from the middle portion of the distillation column will at first pass through the at least one separation stage and thence arrive at the bottom. Below the last separation stage in the lower section of the distillation column, a stream is removed, run through a reboiler, which evaporates at least a portion of the stream, and then at least partly recycled into the bottom. The reboiler in the distillation column according to the invention especially serves to introduce at least a portion of the energy needed for separation. In a preferred embodiment of the present invention, the stream, after passing through the reboiler, is separated, and a portion thereof is recycled into the bottom of the distillation column, and the other portion is discharged from the process as high boilers. It is alternatively possible that the high boiler is taken directly from the bottom of the distillation column, i.e. without prior separation, and discharged from the process. In that case, it could be fed, for example, to a thermal utilization.

The medium boiler intermediate obtained from the separating-off of the low boilers and the high boilers in step a) is then guided to a sorption unit in step b) in order to at least partly remove residual low boilers and residual high boilers from the stream, and to hydrogenate at least a portion of the (low-boiling, medium-boiling or high-boiling) olefins present. A purified hydrocarbon stream is then obtained from this step b), containing more than 98% by weight, preferably more than 99% by weight, more preferably more than 99.5% by weight, of $C_x$ alkanes. In a preferred embodiment of the present invention, the purified hydrocarbon stream obtained from step b) contains not more than 2% by weight, preferably not more than 1% by weight, more preferably not more than 0.5% by weight, of Cx+1 hydrocarbons. Further preferably, the purified hydrocarbon stream obtained from step b) contains not more than 200 ppm by weight of Cx olefin. If the process purifies a C3 hydrocarbon stream, what is preferably obtained is a propane stream containing not more than 2% by weight, preferably not more than 1% by weight, more preferably not more than 0.5% by weight, of C4 hydrocarbons, especially isobutane and n-butane. The propane stream then also preferably contains not more than 200 ppm by weight of propene.

In order to hydrogenate a sufficient portion of the olefins in step b), an appropriate amount of hydrogen is added. The exact amount can be determined by the desired reaction. This is familiar to those skilled in the art. The hydrogen may be metered into the medium boiler intermediate in the feed to the sorption unit. In order to assure sufficient solubility of the hydrogen, the olefin content in the medium boiler intermediate should not exceed 5% by weight. This can be effected either by suitable raw material selection of the hydrocarbon stream to be purified or by appropriate separating-off of the olefins in the upstream step a).

The sorption in step b) is especially conducted with a suitable sorbent. The sorbent used with preference in accordance with the invention comprises a porous carrier material, especially $SiO_2$, coated with nickel and tin oxide on its surface. Graphite may be used as lubricant in the shaping and may therefore likewise be present. Other components, for example traces of titanium dioxide or aluminium oxide, may be present for production-related reasons.

The sorbent may accordingly have the following composition that adds up to 100% by weight:
  nickel: 15% to 65% by weight;
  zinc oxide: 5% to 40% by weight;
  silicon dioxide: 5% to 75% by weight;
  graphite: 0% to 5% by weight;
  other components 0% to 1% by weight.

The carrier material used is preferably precipitated silica. The fine particle distribution and the high specific surface area result in pyrophoric properties in elemental nickel, meaning that the sorbent can self-ignite at 20° C. under an air atmosphere. This complicates the handling of the sorbent, but enhances its effectiveness. Consequently, the use of an $Ni/ZnO/SiO_2$-based system with pyrophoric properties as sorbent is preferred.

The pyrophoric properties arise especially when a metallic nickel surface area of at least 3 $m^2/g$ is provided, based on the nickel content of the sorbent. This promotes adsorptive action and at the same time gives rise to the pyrophoric properties. Surface area is measured by hydrogen chemisorption. Preference is thus given to using a sorbent having a metallic nickel surface area of greater than 3 $m^2/g$, preferably of greater than 5 $m^2/g$, more preferably of greater than 7 $m^2/g$, based in each case on the total weight of nickel in the sorbent.

In order to activate the $Ni/ZnO/SiO_2$ system which is used as sorbent, it should be purged or reduced prior to use with a hydrogen stream at a temperature of 150° C. to 400° C., preferably 180° C. to 280° C., especially 200° C. to 240° C.

The activation with hydrogen can be effected in situ or ex situ, i.e. at the site of later use or removed therefrom, after the production of the sorbent. If the sorbent is deactivated, it can be reactivated again by a further hydrogen purge.

One example of a suitable sorbent is the Octolyst® H10126 catalyst, available from Evonik Industries AG. A particular advantage of the process is therefore that the sorbent used for the sorption in step b) is commercially available as catalyst and therefore does not have to be produced first. The sorbent is typically supplied in an oxidized state, which permits handling at room temperature under air. Before use, the sorbent must therefore be activated as mentioned by a subsequent reduction with hydrogen. After use, the sorbent must be stabilized by oxidation with air, such that it can be removed in a simple manner.

If the sorbent is not to be bought in, production thereof can in principle be accomplished by the following steps:
1. providing a porous framework material composed of silicon dioxide;
2. blending the framework material with nickel carbonate and zinc oxide;
3. thermal breakdown of the nickel carbonate to NiO;
4. reduction with supply of hydrogen to metallic nickel.

In order to avoid exothermicity spikes, steps 3. and 4. can also be effected in one step, since 3 is endothermic and 4. is strongly exothermic. In a preferred embodiment, the nickel carbonate used ($NiCO_3$) is thus broken down thermally in one step, and NiO formed in parallel is reduced with hydrogen to metallic nickel. In a second embodiment, the two steps can be effected separately. In both cases, the activation can also be accomplished using a mixture of nitrogen and hydrogen, the hydrogen content of which is increased in the course of activation.

The sorbent is preferably poured in as a bed in a reactor, and the hydrocarbon mixture to be purified flows through it. Corresponding plant arrangements are known to the person skilled in the art. Compliance with a particular temperature during sorption in step b) can be influential in terms of the purifying capacity of the sorbent. It is advantageous when the temperature in the sorption in step b) of the process according to the invention is between 10° C. and 150° C., preferably between 20° C. and 130° C., and more preferably between 30° C. and 120° C.

In order to achieve particularly effective purification and to avoid interruptions to operation resulting from exchange of the sorbent, it is advisable to use a plurality of reactors which can be connected in a revolving manner in such a way that there is always a reactor with sufficient fresh sorbent that can be utilized for step b). In this case, without interrupting the stream to be purified, at least one vessel can be taken out and the material present therein can be rinsed and removed, followed by refilling in an analogous manner.

What is important is that the intermediate obtained from step a) is exclusively in the liquid state during contact with the sorbent. Within the specified temperature range, this is especially assured by a pressure between 5 to 35 bar. However, the pressure is ultimately unimportant, provided that the intermediate is in the liquid state. The weight hourly space velocity (WHSV) is then preferably selected between 0.5 and 15 $h^{-1}$. The beds consist of a bed of the respective sorbent having a bulk density in the range from 0.7 to 1.5 $kg/m^3$, preferably about 1.15 $kg/m^3$.

The impurities that are to be removed in accordance with the invention from the intermediate obtained from step a) are preferably organic sulfur compounds that act as catalyst poison in the subsequent workup of the hydrocarbon mixture. Catalyst-damaging organic sulfur compounds present in the raw material streams that are typically obtainable especially include thiols having the general formula R-SH, disulfides having the general formula R-S-S-R', sulfides having the general formula R-S-R', and substituted or unsubstituted sulfur-containing heterocycles, such as, in particular, thiophenes and/or thiolanes. In the above-specified structural formulae, R and R' may be identical or different alkyl, aryl, cycloalkyl or alkenyl radicals, where R and R' are especially methyl, ethyl, propyl, butyl, phenyl, cyclohexyl or butenyl radicals.

The sorption of the aforementioned impurities is irreversible. For that reason, the sorbent used in accordance with the invention cannot be regenerated. This means that highly contaminated streams rapidly exhaust the sorbents, such that they have to be exchanged. In the interests of economically viable operation of the purifying process, the proportion by weight of the contaminants in the contaminated hydrocarbon mixture, based on the total weight thereof, should preferably be less than 0.2% by weight. More preferably, the contaminated hydrocarbon mixture contains less than 100 ppm by weight and more preferably less than 10 ppm by weight of impurities, in each case calculated as sulfur atom. In the case of such a low level of contamination, the sorbent can be operated for a very long period and additionally enables virtually complete removal of the catalyst poisons. The upstream separating-off of low and high boilers in accordance with the invention results in such a low degree of contamination since particular low- and high-boiling sulfur compounds can be separated from the Cx stream even there, and only very low contents of sulfur compounds arrive at the sorption bed.

Figure 2:
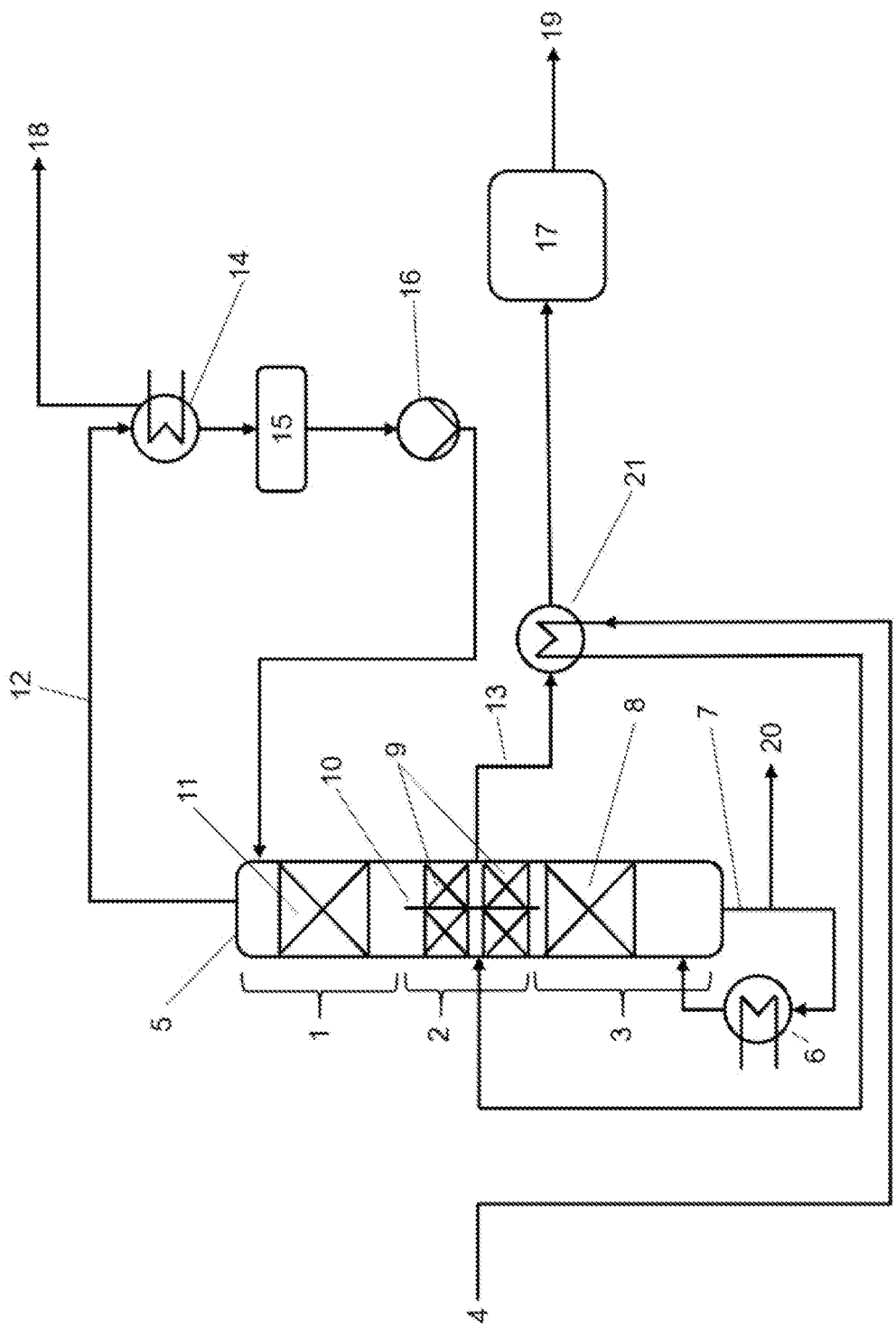
FIG. 2 shows a further embodiment of the present invention.

Preferred illustrative embodiments are shown in the two figures, FIG. 1 and FIG. 2. It will be apparent that the concept according to the invention can also be achieved with other embodiments.

FIG. 1 shows an embodiment of the present invention with a distillation column (5) for the separating-off in step a) and a sorption unit (17) for the sorption in step b). The distillation column (5) has an upper section (1) comprising a separation stage (11), a middle section (2) comprising multiple separation stages (9) and a dividing wall (10), and a lower section (3) likewise comprising a separation stage (8). In the middle section (2), the hydrocarbon stream (4) to be purified is fed in and separated by the process according to the invention. A bottoms fraction (7) is removed at the bottom, a portion of which is removed from the process as high boilers (20). The remaining bottoms fraction is then heated by means of a reboiler (6) and returned to the distillation column (5). This introduces at least a portion of the energy needed for separation into the system. At the top of the distillation column (5), a tops fraction (12) is removed and guided to a condenser (14). The uncondensed fractions are discharged from the process as low boilers (18). The condensed portion is recycled via a vessel (15) and a reflux pump (16) to the upper section (1) of the distillation column (5). The intermediate (13) obtained in the separating-off in step a) is accepted as sidestream and guided to the sorption in the sorption unit (17). The purified hydrocarbon stream (19) is then obtained from the sorption unit.

FIG. 2 shows a further embodiment of the present invention. The sequence and plant features are very substantially identical to FIG. 1. The sole difference is that the hydrocarbon stream (4) to be purified is guided through a heat exchanger (21) before arriving in the distillation column (5). Energy exchange takes place there between the hydrocarbon stream (4) to be purified and the intermediate (13), which heats up the hydrocarbon stream (4) to be purified. In this respect, the heat exchanger (21) should also be regarded as a preheater of the hydrocarbon stream (4) to be purified.

Examples

Example 1 (inventive)

A C3 stream containing 90% by weight of propane, 1.5% by weight of propene, 1% by weight of ethane, 7.5% by weight of isobutane, and 2 mg/kg of sulfur in the form of methanethiol is introduced into a dividing wall column according to the invention. Obtained in the side draw of the column is a prepurified C3 stream containing about 99% by weight of propane and about 1% by weight of propene, and 1.2 mg/kg of sulfur in the form of methanethiol. The mass flow ratio of column feed to side draw is about 1:0.8.

A portion of this side draw is introduced into a downstream fixed reactor bed. Introduced as sorbent into a reaction tube of diameter 1 cm and capacity 23 g is the commercial Octolyst® H 10126 catalyst from Evonik Industries AG, containing about 45% by weight of Ni, about 28% by weight of ZnO, about 25% by weight of $SiO_2$ and about 2% by weight of graphite, in the form of rounded cylindrical 5×5 mm tablets, with a nickel surface area of 9 $m^2/g$ as measured by hydrogen chemisorption. The bulk density is about 1.15 $kg/dm^3$. The adsorbent was activated beforehand in a nitrogen-hydrogen stream at about 220° C., with inclusion initially of 1% by volume of hydrogen and ultimately of 50% by volume of hydrogen according to the exothermicity. Thereafter, the catalyst bed was cooled down in a nitrogen stream.

The bed is brought to a temperature of 30° C. by heating the tube walls, and the mixture from the side draw of the dividing wall column is passed through it at a pressure of 24 bar. The loading of the adsorber beds is 370 g/h, and so the sulfur input is about 0.44 mg/h. A sufficient amount of hydrogen is supplied that it is still soluble under the given conditions.

As shown by the analyses, the sulfur is at first removed virtually quantitatively from the mixture (Table 1). The breakthrough of sulfur occurs after about 600 hours. At that time, the purifying bed has absorbed a total of about 0.27 g of sulfur, corresponding to an absorption of 1.2% by weight, based on the freshly introduced sorbent. Up to the time of sulfur breakthrough, propene was fully hydrogenated.

After the end of this experiment, the bed is purged with warm nitrogen and then cautiously oxidized with cold nitrogen-air mixture until there is essentially no further exothermicity in pure air. The sorbent can be removed essentially intact and with still sufficient stability. The results of the experiment are recorded in Table 1.

TABLE 1

Results for Example 1

| Average S content [% by wt.] in feed | Average S content [% by wt.] in output up to 600 h | Average decrease in S [% by wt.] in output compared to feed up to 600 h |
| --- | --- | --- |
| 0.00012 | 0.000003 | 97.5 |

The invention claimed is:

1. A process for purifying a hydrocarbon stream comprising at least a $C_x$ alkane, a $C_x$ olefin, low boilers comprising $C_{x-1}$ hydrocarbons and high boilers comprising $C_{x+1}$ hydrocarbons, wherein x is 3 or 4, the process comprising:

a) separating off at least a portion of the low boilers and separating off at least a portion of the high boilers in a single distillation column, to obtain an intermediate;
b) removing at least a portion of remaining low boilers and/or at least a portion of remaining high boilers from the intermediate obtained from a) by sorption in a sorption unit, to obtain a purified hydrocarbon stream containing more than 98% by weight of the $C_x$ alkane, wherein the sorption in b) is conducted in the presence of hydrogen, and
wherein a hydrogenation of at least a portion of olefins present additionally takes place in the sorption unit.

2. The process according to claim 1, wherein the hydrocarbon stream is a $C_3$ hydrocarbon stream.

3. The process according to claim 1, wherein the distillation column consists of
an upper section comprising a top of the distillation column and at least one first separation stage,
a middle section comprising at least one second separation stage, and
a lower section comprising a bottom of the distillation column and at least one third separation stage.

4. The process according to claim 3, wherein the distillation column is a dividing wall column having a dividing wall in the middle section, which divides the middle section into a feed section and an outlet section.

5. The process according to claim 4, wherein the intermediate obtained from the separating-off in a) is removed via a side draw in the outlet section of the dividing wall column.

6. The process according to claim 4, wherein the hydrocarbon stream to be purified is fed in the feed section of the dividing wall column.

7. The process according to claim 4, wherein a stream containing the low boilers is removed via the top of the column in the dividing wall column, and a stream containing the low boilers is removed via the bottom of the column.

8. The process according to claim 7, wherein the stream containing the low boilers removed at the top of the column is guided to a condenser and at least partly condensed.

9. The process according to claim 8, wherein an uncondensed portion of the stream containing the low boilers is discharged from the process.

10. The process according to claim 8, wherein a condensed portion of the stream containing the low boilers is recycled to the dividing wall column.

11. The process according to claim 10, wherein a recycled condensed portion of the stream containing the low boilers is introduced into the at least one first separation stage of the upper section of the distillation column.

12. The process according to claim 4, wherein the hydrocarbon stream to be purified passes through a heat exchanger and is preheated before the hydrocarbon stream is fed to the dividing wall column.

13. The process according to claim 12, wherein heating in the heat exchanger is effected by heat exchange with the intermediate.

14. The process according to claim 1, wherein the sorbent unit comprises a sorbent comprising a porous carrier material coated with nickel and tin oxide on a surface.

15. The process according to claim 14, wherein the sorbent has the following composition that adds up to 100% by weight:
15% to 65% by weight of nickel;
5% to 40% by weight of zinc oxide;
5% to 75% by weight of silicon dioxide;
0% to 5% by weight of graphite; and
0% to 1% by weight of an additional component.

16. The process according to claim 14, wherein the porous carrier material is $SiO_2$.

\* \* \* \* \*